US011313224B2

(12) United States Patent
Hakami et al.

(10) Patent No.: US 11,313,224 B2
(45) Date of Patent: Apr. 26, 2022

(54) THERMAL MATURITY DETERMINATION OF ROCK FORMATIONS USING MUD GAS ISOTOPE LOGGING

(71) Applicant: Saudi Arabian Oil Company, Dhahran (SA)

(72) Inventors: Ahmed Hakami, Dhahran (SA); Leroy Ellis, Dhahran (SA); Sami Abdelbagi, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 230 days.

(21) Appl. No.: 15/430,049

(22) Filed: Feb. 10, 2017

(65) Prior Publication Data

US 2017/0226851 A1  Aug. 10, 2017

Related U.S. Application Data

(60) Provisional application No. 62/293,498, filed on Feb. 10, 2016.

(51) Int. Cl.
*E21B 49/00* (2006.01)
*G01V 9/00* (2006.01)
(Continued)

(52) U.S. Cl.
CPC ............ *E21B 49/005* (2013.01); *E21B 47/07* (2020.05); *E21B 49/02* (2013.01); *E21B 49/087* (2013.01);
(Continued)

(58) Field of Classification Search
CPC .... E21B 49/005; E21B 49/087; E21B 47/065; E21B 49/02
See application file for complete search history.

(56) References Cited

U.S. PATENT DOCUMENTS 8,714,246 B2   5/2014  Pop et al.
8,967,249 B2   3/2015  Akkurt et al.
(Continued)

FOREIGN PATENT DOCUMENTS

CN   104730595 A   6/2015
CN   105242026 A   1/2016

OTHER PUBLICATIONS

Jerry J. Sweeney.,"Evaluation of a Simple Model of Vitrinite Reflectance Based on Chemical Kinetics"., The American Association of Petroleum Geologists Bulletin V. 74, No. 10 (Oct. 1990), p. 1559-1570 (Year: 1990).*

(Continued)

*Primary Examiner* — Yoshihisa Ishizuka
(74) *Attorney, Agent, or Firm* — Bracewell LLP; Constance G. Rhebergen; Brian H. Tompkins

(57) ABSTRACT

Systems and methods for determining the thermal maturity of a rock formation from isotopic values in gases are provided. Isotope values may be obtained from mud gas isotope logging, vitrinite reflectance equivalence values may be determined from core samples using known techniques. A relationship between vitrinite reflectance equivalence and isotopic values, such as carbon-13 methane values, may be determined. The vitrinite reflectance equivalence may then be determined from isotopic values to determine the thermal maturity of rock formations accessed by drilling additional exploration wells.

16 Claims, 11 Drawing Sheets

(51) Int. Cl.
*G01N 33/28* (2006.01)
*G01V 5/06* (2006.01)
*E21B 47/07* (2012.01)
*E21B 49/02* (2006.01)
*E21B 49/08* (2006.01)

(52) U.S. Cl.
CPC .......... *G01N 33/2823* (2013.01); *G01V 5/06* (2013.01); *G01V 9/007* (2013.01)

(56) References Cited

U.S. PATENT DOCUMENTS

| | | | |
|---|---|---|---|
| 9,029,156 B2 | 5/2015 | Kornacki et al. | |
| 9,429,554 B2 | 8/2016 | Williams et al. | |
| 2004/0019437 A1* | 1/2004 | Kelemen | G01N 33/241 702/27 |
| 2005/0082473 A1* | 4/2005 | Socki | H01J 49/0468 250/288 |
| 2005/0256646 A1 | 11/2005 | Ellis | |
| 2010/0095742 A1* | 4/2010 | Symington | E21B 41/0064 73/23.35 |
| 2011/0088895 A1* | 4/2011 | Pop | E21B 7/04 166/254.2 |
| 2013/0270011 A1* | 10/2013 | Akkurt | E21B 49/088 175/58 |
| 2013/0273661 A1 | 10/2013 | Pomerantz | |
| 2014/0238670 A1 | 8/2014 | Pop et al. | |
| 2014/0256055 A1* | 9/2014 | Pottorf | G01V 9/007 436/163 |
| 2015/0198577 A1* | 7/2015 | Williams | G01N 33/24 250/282 |
| 2015/0240633 A1 | 8/2015 | Akkurt et al. | |
| 2015/0323516 A1 | 11/2015 | Washburn | |
| 2016/0084045 A1 | 3/2016 | Lawson et al. | |
| 2016/0084081 A1 | 3/2016 | Lawson et al. | |
| 2016/0084817 A1* | 3/2016 | Lawson | G01V 9/007 702/6 |
| 2016/0139293 A1* | 5/2016 | Misra | G01V 3/30 702/7 |

OTHER PUBLICATIONS

Juliao,Tatiana "The role of solid bitumen in the development of porosity in shale oil reservoir rocks of the Upper Cretaceous in Colombia"., International Journal of Coal Geology 147-148 (2015) 126-144 (Year: 2015).*

Ni, Yunyan., "Using carbon and hydrogen isotopes to quantify gas maturity, formation temperature, and formation age—specific applications for gas fields from the Tarim Basin, China"., Energy Exploration & Exploitation • vol. 30 • No. 2 • 2012 pp. 273-294 (Year: 2012).*

Zou, Yan-Rong., "Variations of natural gas carbon isotope-type curves and their interpretation—A case study"., Organic Geochemistry 38 (2007) 1398-1415 (Year: 2007).*

Schimmelmanna, Arndt., "Experimental controls on D/H and 13C/12C ratios of kerogen, bitumen and oil during hydrous pyrolysis"., Organic Geochemistry 32 (2001) 1009-1018 (Year: 2001).*

International Search Report and Written Opinion for International Application No. PCT/US2017/017306; International Filing Date Feb. 10, 2017; dated May 19, 2017; pp. 1-11.

Sherwood, Owen A. et al.; "Hydrocarbon Maturity and Migration Analysis Using Production Gas Stable Isotopic Signatures in the Wattenberg Field, Denver Basin, Colorado, USA" URTeC: 1580285, Unconventional Resources Technology Conference, 2013; pp. 1-7.

* cited by examiner

THERMAL MATURITY DETERMINATION OF ROCK FORMATIONS USING MUD GAS ISOTOPE LOGGING

PRIORITY CLAIM

This application claims priority to U.S. Provisional Application No. 62/293,498, filed Feb. 10, 2016, and titled "Mud Gas Isotope Logging Application for Sweet Spot Identification in an Unconventional Shale Gas Play; a Case Study from Jurassic Carbonate Source Rocks in Jafurah Basin, Saudi Arabia," a copy of which is incorporated by reference in its entirety for the purposes of United States patent practice.

BACKGROUND

Field of the Disclosure

Embodiments of the disclosure generally relate to the drilling and extraction of oil, natural gas, and other resources, and more particularly to the evaluation of geological formations and identification of resources in such geological formations.

Description of the Related Art

Oil, gas, and other natural resources are used for numerous energy and material purposes. The search and extraction of oil, natural gas, and other subterranean resources from the earth may cost significant amounts of time and money. The difficulty and costs associated with the extraction of some resources, such as shale gas, may increase the challenged in evaluating potential drilling locations such as basins and identifying the "sweet spots" in such locations that enable economically viable production of such resources. Existing techniques may be unable to accurately distinguish between different rock formations in some locations, thus limiting information available for selection of drilling sites and subsequent production capability. Some techniques, such as core sampling, may be inefficient and may result in significant increases in development time and costs.

SUMMARY

Well logging techniques may provide for the evaluation of rock formations, including rock formations in basins or other features potentially having extractable shale gas. One or more exploratory wells may be drilling in a geographic feature, and well logging may be performed in each well to evaluate differences in rock formations and potential drilling sites. Such well logging may include core logging, mud logging, and mud gas isotope logging (MGIL).

MGIL involves direct isotopic and compositional measurements of formation gases sampled from the circulating mud stream during drilling. MGIL may provide measurements of carbon and hydrogen isotope data in various gases such as methane, propane, ethane, and so on.

One estimation performed by geochemical tools is the determination of the thermal maturity of rock formations. In conventional systems, the thermal maturity of a rock formation is extremely difficult to estimate once hydrocarbons are expelled from the source rock and begin to migrate along porous conduits that can range from tens of meters to hundreds of kilometers in length, thus irrevocably altering the chemical signature of the hydrocarbons. These changes are the result of many different processes, such as mixing with secondary contributors, gravity and density segregation, and distillation. In some instances, hydrocarbon generation kinetics may be derived using laboratory pyrolysis of source rock samples to model subsurface conditions and quantity resultant hydrocarbon products that are generated; however, such techniques require representative source rock samples that are difficult to obtain and may instead may use poor quality analogue samples. Moreover, conventional systems are difficult to check the model accuracy against field data from the source rock.

As explained herein, the use of MGIL with shale formations may result in the correlation of in situ thermal maturity of rock formations with the compositional and isotopic products of associated hydrocarbon generation, thus making the samples accurately representative and self-sourcing.

In one embodiment, a method for determining the thermal maturity of a rock formation in a geological region of interest for hydrocarbon production is provided. The method includes drilling a plurality of exploration wells to access the rock formation and obtaining mud gas isotope logging data for each of the plurality of exploration wells. The mud gas isotope logging data includes isotopic values associated with an isotope in a mud gas. The method also includes obtaining a vitrinite reflectance equivalent for each of the plurality of exploration wells and determining a relationship between vitrinite reflectance equivalent and the isotopic values, the vitrinite reflectance equivalent indicating a thermal maturity of the rock formation.

In some embodiments, the method includes determining the vitrinite reflectance equivalent using the relationship and isotopic values associated with an additional exploration well accessing a second rock formation and identifying a thermal maturity of the second rock formation using the vitrinite reflectance equivalent. In some embodiments, the method includes identifying a drilling location in the geological region of interest for hydrocarbon production using the thermal maturity indicated by the vitrinite reflectance equivalent. In some embodiments, the mud gas comprises methane and the isotope comprises carbon-13. In some embodiments, the mud gas comprises hydrogen and the isotope comprises deuterium. In some embodiments, the obtaining the vitrinite reflectance equivalent for each of the plurality of exploration wells includes determining, for each of the plurality of exploration wells, a temperature at which the maximum rate of hydrocarbon generation occurs in a kerogen sample from the respective exploration well during a pyrolysis analysis and calculating the vitrinite reflectance equivalent from the temperature for each of the plurality of exploration wells. In some embodiments, obtaining the vitrinite reflectance equivalent for each of the plurality of exploration wells includes determining an amount of bitumen in a core sample obtained from the respective exploration well and calculating the vitrinite reflectance equivalent from the bitumen amount for each of the plurality of exploration wells. In some embodiments, determining a relationship between vitrinite reflectance equivalent and the isotopic values includes performing a least squares regression analysis on a set of vitrinite reflectance equivalent values and a set of isotopic values.

In another embodiment, a system for determining the thermal maturity of a rock formation in a geological region of interest for hydrocarbon production is provided. The system includes mud gas isotope logging system configured to receive mud gas and determine isotopic values of associated with an isotope in the mud gas and a thermal maturity determination processing system having a processor and a non-transitory computer-readable memory accessible by the processor, the memory having executable code stored thereon. The executable code comprising a set of instructions that causes the processor to perform operations that include receiving, from the mud gas isotope logging system, mud gas isotope logging data for each of a plurality of exploration wells, the mud gas isotope logging data comprising isotopic values associated with the isotope in the mud gas and obtaining a vitrinite reflectance equivalent for each of the plurality of exploration wells, the vitrinite reflectance equivalent determine from a core sample from each of the plurality of exploration wells. The operations also include determining a relationship between vitrinite reflectance equivalent and the isotopic value, the vitrinite reflectance equivalent indicating a thermal maturity of the rock formation.

In some embodiments, the operations further include determining a vitrinite reflectance equivalent associated with an additional exploration well using the relationship and an isotopic value associated with the additional exploration well and identifying a thermal maturity of the rock formation using the vitrinite reflectance equivalent. In some embodiments, the mud gas comprises methane and the isotope comprises carbon-13. In some embodiments, the mud gas comprises hydrogen and the isotope comprises deuterium. In some embodiments, obtaining a vitrinite reflectance equivalent for each of the plurality of exploration wells includes determining, for each of the plurality of exploration wells, a temperature at which the maximum rate of hydrocarbon generation occurs in a kerogen sample from the respective exploration well during a pyrolysis analysis and calculating the vitrinite reflectance equivalent from the temperature for each of the plurality of exploration wells. In some embodiments, obtaining a vitrinite reflectance equivalent for each of the plurality of exploration wells includes determining an amount of bitumen in a core sample obtained from the respective exploration well and calculating the vitrinite reflectance from the bitumen amount for each of the plurality of exploration wells. In some embodiments, determining a relationship between vitrinite reflectance equivalent and the isotopic values comprises performing a least squares regression analysis on a set of vitrinite reflectance equivalent values and a set of isotopic values.

In another embodiment, another method for determining the thermal maturity of a rock formation in a geological region of interest for hydrocarbon production is provided. The method includes obtaining a carbon-13 isotopic value from a mud gas isotope logging system, the carbon-13 isotopic value associated with a mud gas, determining a vitrinite reflectance equivalent from the carbon-13 isotopic value, and comparing the vitrinite reflectance equivalent to a range of vitrinite reflectance values to identify a thermal maturity of the rock formation. IN some embodiments, the mud gas is methane. In some embodiments, the method includes identifying a drilling location in the geological region of interest for hydrocarbon production using the thermal maturity.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
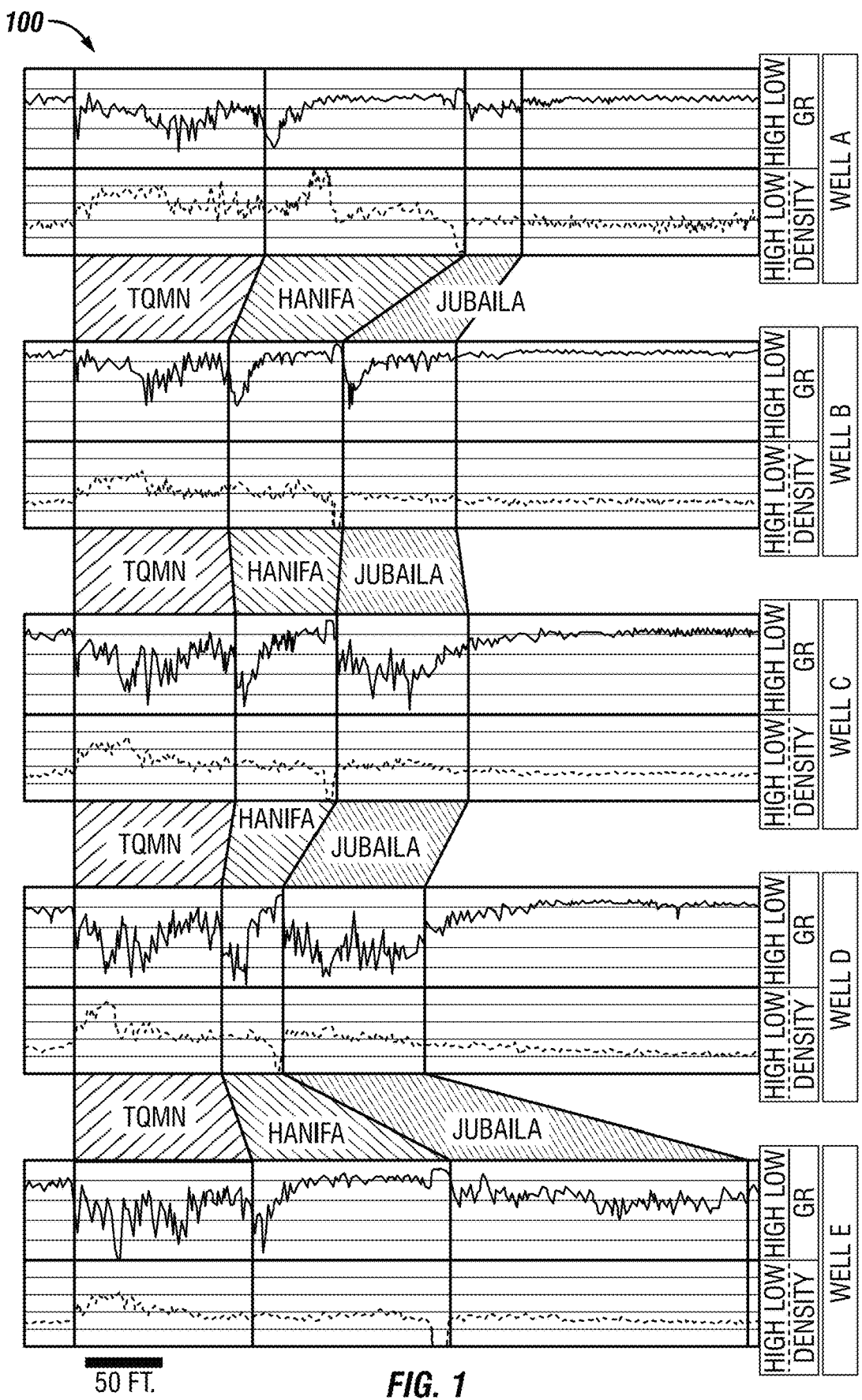
FIG. 1 depicts measurement-while-drilling gamma ray (GR) and density logs of stratigraphic cross-sections for the five exploratory wells drilled in a geographic region of interest in accordance with embodiments of the disclosure.

The present disclosure will now be described more fully hereinafter with reference to the accompanying drawings, which illustrate embodiments of the disclosure. This disclosure may, however, be embodied in many different forms and should not be construed as limited to the illustrated embodiments set forth herein. Rather, these embodiments are provided so that this disclosure will be thorough and complete, and will fully convey the scope of the disclosure to those skilled in the art.

Embodiments of the disclosure include systems and methods for determining the thermal maturity of a rock (e.g., shale) formation having hydrocarbon (e.g., shale gas) resources. In some embodiments, two or more exploration wells may be drilled in a geographic region of interest. Mud gas isotope logging (MGIL) may be performed on the two or more exploration wells, and isotopic values in mud gas may be determined. As used herein, the term "isotopic values" refers to a value corresponding to or indicative of the amount of an isotope. The isotopic value may refer to an "isotopic signature" as known in the art and as calculated with respect to a Pee Dee Belemnite (PDB) standard. For example, the isotopic values of various carbon and hydrogen isotopes in mud gases such as methane (C1), ethane (C2), propane (C3), butane (C4), and pentane (C5) may be determined. The vitrinite reflectance equivalent may be determined for rock formations in the exploration wells from core samplings using known techniques. For example, in some embodiments, the temperature at which the maximum rate of hydrocarbon generation during pyrolysis analysis occurs in a kerogen sample obtained from the well may be determined, and the vitrinite reflectance equivalent may be determined from this maximum temperature. In other embodiments, the vitrinite reflectance equivalent may be additionally or alternatively calculated from solid bitumen present in core samples. Next, relationship between vitrinite reflectance equivalent, as an indicator of thermal maturity, and the isotopic values of a selected isotope analyzed via the MGIL may be determined. The thermal maturity of rock formations may then be determined from isotopic values from MGIL in additional exploration wells without performing core sampling or other costly or time-consuming techniques on such wells. Advantageously, the MGIL and subsequent thermal maturity determination may be performed while drilling such exploration wells to avoid other techniques that may delay drilling and increase drilling time.

EXAMPLES

The following examples are included to demonstrate embodiments of the disclosure. It should be appreciated by those of skill in the art that the techniques and compositions disclosed in the example which follows represents techniques and compositions discovered to function well in the practice of the disclosure, and thus can be considered to constitute modes for its practice. However, those of skill in the art should, in light of the present disclosure, appreciate that many changes can be made in the specific embodiments which are disclosed and still obtain a like or a similar result without departing from the spirit and scope of the disclosure Five wells (referred to as Well-A, Well-B, Well-C, Well-D, and Well-E) were drilled in a basin suspected as a source of shale gas and having middle-to-upper Jurassic organic-rich carbonate mudrocks. The wells were used to evaluate three potential source rock targets at different depths and referred to as Tuwaiq, Hanifa, and Jubaila. The wells were drilled vertically, cored, logged, and sampled to obtain the data discussed herein. The coring operations were performed to obtain a sufficient number of core samples to enable detailed source rock and maturity characterization across the three source rock targets. As explained below, mud gas isotope logging (MGIL) and source rock data were used to assess the thermal maturity of hydrocarbon shows, and both datasets were used to determine an accurate thermal maturity for thermal maturity estimation.

FIG. 1 depicts measurement-while-drilling gamma ray (GR) and density logs 100 of stratigraphic cross-sections for the five wells Well-A, Well-B, Well-C, Well-D, and Well-E. The logs 100 in FIG. 1 illustrate the lateral correlation of individual lithofacies within the middle and upper Jurassic source rock intervals. The laminated, organic-rich lime mudstone source rocks are relatively thick (up to 400 feet (ft)) and extend over large geographical areas. As explained below, the acquired source rock indicated that the Jubaila formation in the basin possesses good source rock quality while the Hanifa formation in the basin possesses poor litho-organic facies.

A data acquisition program was performed to acquire data on the three source rock targets. Core analysis was performed to capture full formation-thick cores across the source rocks to enable detailed characterization. As noted above, mud logs and MGIL were also performed to assess the type, origin, and thermal maturity of hydrocarbon shows.

The core intervals were selected by seismic data and correlation with historical offset wells. During drilling of the five wells, coring points were selected using near-bit measurement-while-drilling gamma ray (MWD GR) tools to identify formation tops. The core interval selection also enabled the capture of portions of the overlying and underlying formations to accurately select the transitions across formations while eliminating the risk of missing the targeted source rock intervals. The short cored intervals also provided data for future sedimentological work to enable analysis of the depositional history and engineering information on fracture growth behavior. RockEval® pyrolysis and LECO® were performed to identify source rock intervals and evaluate their quality (generative potential) and associated thermal maturity. The source rock maturity was also determined in some wells by direct organic petrographic analysis measuring the vitrinite reflectance (%% Ro) and other organic matter maceral-type reflectance.

The core analysis was performed on about seven hundred core samples collected from the five exploration wells: Well-A, Well-B, Well-C, Well-D, and Well-E. Table 1 summarizes the average geochemical properties for the three source rock formations Tuwaiq, Hanifa, and Jubaila explored by the five exploration wells. The average geochemical properties include total organic carbon (TOC) content, S1 pyrolysis yield (the S1 peak in a pyrolysis analysis such as RockEval®), S2 pyrolysis yield (the S2 peak in a pyrolysis analysis such as RockEval®), hydrogen index, and the temperature (Tmax) at which the maximum rate of hydrocarbon generation occurred in a kerogen sample during a pyrolysis analysis:

TABLE 1

Average Geochemical Properties in Source Rock Formations

| Geochemical Attributes | | Source Rock Formation | | |
| --- | --- | --- | --- | --- |
| | | Jubaila | Hanifa | Tuwaiq |
| Total Organic Carbon Content (wt %) | Maximum | 4.98 | 3.9 | 13.17 |
| | Minimum | 1.00 | 0.15 | |
| | Average | 2.44 | 1.19 | 4.9 |
| S1 Pyrolysis Yield (mg HC/g rock) | Maximum | 4.69 | 4.58 | 12.04 |
| | Minimum | 0.32 | 0.02 | 0.39 |
| | Average | 1.05 | 0.77 | 3.4 |
| S2 Pyrolysis Yield (mg HC/g rock) | Maximum | 7.55 | 6.18 | 18.8 |
| | Minimum | 0.55 | 0.02 | 0.54 |
| | Average | 2.53 | 0.8 | 3.4 |
| Hydrogen Index (S2*100/TOC) | Maximum | 231 | 218 | 194 |
| | Minimum | 63 | 50 | 48 |
| | Average | 112 | 102 | 91 |
| Tmax (° C.) | Maximum | 476 | 479 | 493 |
| | Minimum | 434 | 456 | 455 |
| | Average | 462 | 471 | 475 |

As shown in Table 1, the source rock formations Tuwaiq and Jubaila possess high source rock quality, whereas source rock formation Hanifa possesses low potential source facies. Thus, the subsequent experiments performed and described herein focused on the source rock formations Tuwaiq and Jubaila as primary and secondary targets for shale gas exploration.

Figure 2A:
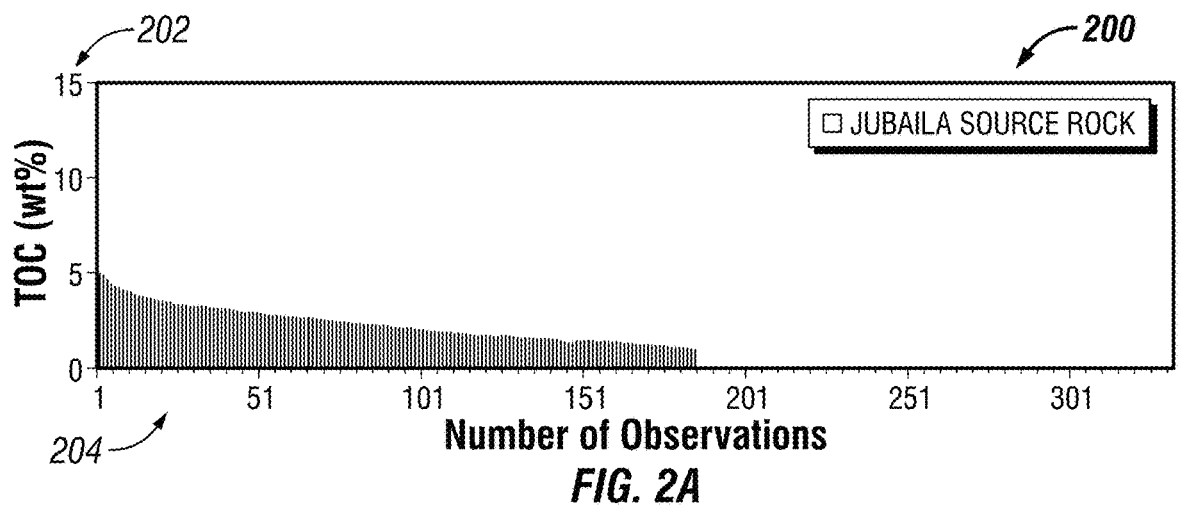
FIGS. 2A-2C are graphs of the distribution of total organic carbon (TOC) for three source rock formations in a geographic region of interest in accordance with embodiments of the disclosure.
Figure 2B:
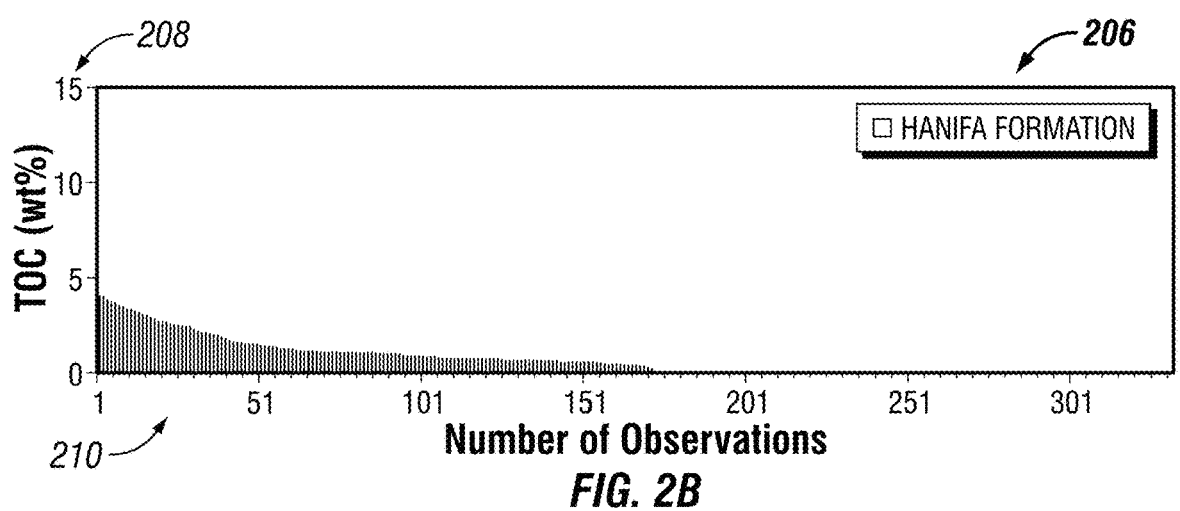
Figure 2C:
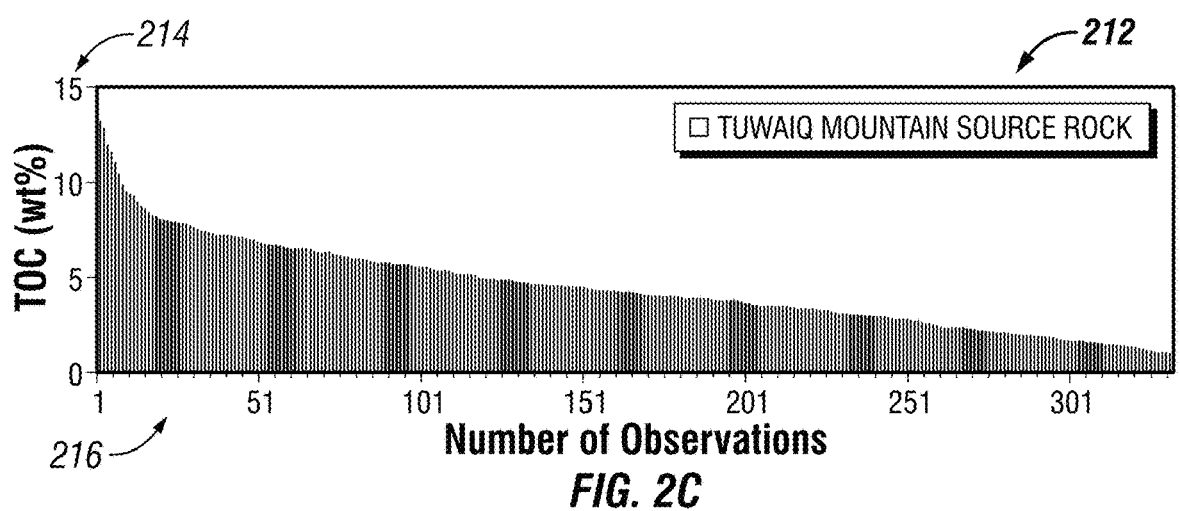

FIGS. 2A-2C are graphs that depict the distribution of total organic carbon (TOC) for the three source rock formations Tuwaiq, Hanifa, and Jubaila. FIG. 2A depicts a graph 200 of TOC wt % (on the y-axis 202) vs. depth (on the x-axis 204) for source rock formation Jubaila. FIG. 2B depicts a graph 206 of TOC wt % (on the y-axis 208) vs. depth (on the x-axis 210) for source rock formation Hanifa. FIG. 2C depicts a graph 112 of TOC wt % (on the y-axis 214) vs. depth (on the x-axis 216) for source rock formation Tuwaiq.

As shown in FIG. 2C, the graph 212 for the Tuwaiq source rock formation illustrates cyclic total organic carbon (TOC) distributions most likely due to fluctuations in relative sea level. The average TOC values of 4.9% and maximum TOC values of 13.17% confirm the potential of the Tuwaiq source rock for production. At present depth and present day thermal maturity, the Tuwaiq source rock has hydrogen indices of 48 mg HC/g TOC to 194 mg HC/g TOC that suggests a type II and type III source rock. As shown in the stratigraphic cross section shown in FIG. 1, the thickness of the Tuwaiq rock formation is relatively uniform between the exploration wells with a slight increase in thickness noted toward the west at Well-A.

In addition to the core sampling, MGIL sampling was performed on each on the five exploration wells: Well-A, Well-B, Well-C, Well-D, and Well-E to enable capture of representative gases from the source rock formations. The MGIL sampling collected one sample about every 150 feet (ft) in the nonproductive zones to establish a background gas trend. Once the background was established, the MGIL sampling interval was decreased to about 500 ft or greater on subsequent wells. During gas shows, the sampling interval was increased to about one sample every 30 ft of penetration. The isotopic ratio of the different gas components were analyzed using an isotope ratio mass spectrometer (IRMS).

The accuracy of the pre-drilling seismic estimated tops and formation thicknesses was compared to the actual stratigraphic depths encountered during drilling of the exploration wells to determine the number of representative gas samples obtained. As the Hanifa rock was found to be a predominantly non-source facies, a minimum number of samples were selected for isotopic analysis for this source rock. For thicker intervals, the top, middle, and bottom-third portions of the source rock were sampled. In some instances, such as the Jubaila rock in exploration wells Well-A and Well-B, the source interval (excluding poor or non-source facies) was found to be non-existent or insufficiently resolved. The isotopic data not present in Table 2 was the result of non-selection or, in some instances such as deuterium analysis, a gas component concentration below the analytical minimum. Table 2 depicts carbon-13 isotopic data in methane ($\delta^{13}C_1$), ethane ($\delta^{13}C_2$), propane ($\delta^{13}C_3$), i-butane ($\delta^{13}iC_4$), n-butane ($\delta^{13}nC_4$), i-pentane ($\delta^{13}iC_5$), and n-pentane ($\delta^{13}iC_5$) for the three source rock formations Hanifa, Source T, and Jubaila and the five exploratory wells, with the isotopic data expressed as delta ($\delta$) deviation of a sample relative to the Pee Dee Belemnite (PDB) reference standard. Table 3 depicts deuterium isotopic data in methane ($\delta DC_1$), ethane ($\delta DC_2$), propane ($\delta DC_3$) for the three source rock formations Hanifa, Source T, and Jubaila and the five exploratory wells, with the isotope data expresses as delta ($\delta$) deviation of sample relative to the PDB reference standard:

TABLE 2

Carbon isotopic data for Hanifa, Source T, and Jubaila formations and Well-A, Well-B, Well-C, Well-D, and Well-E exploratory wells

| Well | Sample No. | Source Rock Formation | $\delta^{13}C_1$ | $\delta^{13}C_2$ | $\delta^{13}C_3$ | $\delta^{13}iC_4$ | $\delta^{13}nC_4$ | $\delta^{13}iC_5$ | $\delta^{13}nC_5$ |
|---|---|---|---|---|---|---|---|---|---|
| Well-A | 1 | Hanifa | −59.6 | −41.2 | −30.9 | −30.3 | −27.8 | −28.4 | −28.4 |
| Well-A | 2 | Tuwaiq | −59.7 | −41.1 | −30.6 | −30.0 | −27.7 | −28.7 | −28.3 |
| Well-A | 3 | Tuwaiq | −60.1 | −40.5 | −30.4 | −30.6 | −27.6 | −28.9 | −27.9 |
| Well-B | 1 | Jubaila | −56.1 | −31.1 | −25.8 | −29.5 | −25.1 | −27.3 | −25.9 |
| Well-B | 2 | Hanifa | −56.3 | −33.6 | −27.8 | −30.7 | −26.9 | −28.2 | −25.9 |
| Well-B | 3 | Hanifa | −56.1 | −32.1 | −26.7 | −30.5 | −25.6 | −27.2 | −25.1 |
| Well-B | 4 | Tuwaiq | −56.0 | −31.3 | −25.6 | −29.8 | −24.9 | −26.9 | −24.2 |
| Well-C | 1 | Jubaila | −52.8 | −33.7 | −28.0 | −30.1 | −26.9 | −29.2 | −33.4 |
| Well-C | 2 | Jubaila | −53.2 | −33.5 | −28.0 | | | | |
| Well-C | 3 | Jubaila | −56.2 | −33.2 | −27.8 | | −26.8 | −28.4 | −32.8 |
| Well-C | 4 | Hanifa | −56.2 | −31.7 | −26.6 | −30.5 | −26.1 | −28.6 | −34.5 |
| Well-C | 5 | Hanifa | −56.4 | −31.8 | −26.8 | −31.7 | −26.7 | −28.1 | −34.3 |
| Well-C | 6 | Tuwaiq | −55.9 | −30.5 | −25.5 | | | | |
| Well-C | 7 | Tuwaiq | −55.5 | −30.5 | −25.5 | −29.4 | −24.7 | −27.2 | −30.1 |
| Well-C | 8 | Tuwaiq | −56.0 | −30.7 | −25.4 | −30.1 | −24.7 | −27.0 | −31.4 |
| Well-C | 9 | Tuwaiq | −55.7 | −30.5 | −25.3 | | | | |
| Well-D | 1 | Jubaila | −50.2 | −29.7 | −26.8 | −29.7 | −26.1 | −28.7 | −25.2 |
| Well-D | 2 | Jubaila | −50.4 | −30 | −26.3 | −29.4 | −25.9 | −27.7 | −24.8 |
| Well-D | 3 | Jubaila | −50.2 | −30 | −26.3 | −28.9 | −25.6 | −27.3 | −24.1 |
| Well-D | 4 | Hanifa | −52.4 | −30.2 | −26.1 | −29.4 | −25.2 | −27.1 | −24.1 |
| Well-D | 5 | Tuwaiq | −53.8 | −29.8 | −25.9 | −29.8 | −24.8 | −27.1 | −23.9 |
| Well-D | 6 | Tuwaiq | −53.8 | −29.4 | −25.5 | −29.4 | −24.4 | −26.5 | −23.8 |
| Well-D | 7 | Tuwaiq | −54.1 | −29.4 | −25.1 | −29.4 | −24.2 | −26.6 | −23.9 |
| Well-D | 8 | Tuwaiq | −53.7 | −30 | −25.9 | −30 | −24.6 | −26.6 | −24 |
| Well-E | 1 | Jubaila | −50.5 | −30.5 | −27.8 | −31.0 | −26.2 | −29.3 | −25.2 |
| Well-E | 2 | Jubaila | −50.9 | −29.6 | −26.3 | −30.1 | −25.2 | −28.5 | −24.8 |
| Well-E | 3 | Jubaila | −51.0 | −29.1 | −25.3 | −29.2 | −24.1 | −27.7 | −23.7 |
| Well-E | 4 | Hanifa | −56.6 | −28.6 | −24.6 | −30.4 | −22.8 | −26.9 | −22.0 |
| Well-E | 5 | Hanifa | −56.3 | −28.2 | −22.5 | −30.2 | −22.5 | −26.7 | −23.0 |
| Well-E | 6 | Hanifa | −53.0 | −26.5 | −22.7 | −28.8 | −22.0 | −25.9 | −22.6 |
| Well-E | 7 | Tuwaiq | −51.3 | −25.4 | −22.1 | −28.3 | −21.8 | −25.5 | −21.8 |
| Well-E | 8 | Tuwaiq | −51.5 | −25.3 | −22.1 | −28.3 | −21.5 | −25.3 | −22.1 |
| Well-E | 9 | Tuwaiq | −50.7 | −24.4 | −20.8 | | | | |

TABLE 3

Deuterium isotopic data for Hanifa, Source T, and Jubaila formations and Well-A, Well-B, Well-C, Well-D, and Well-E exploratory wells

| Well | Sample No. | Source Rock Formation | $\delta DC_1$ | $\delta DC_2$ | $\delta DC_3$ |
|---|---|---|---|---|---|
| Well-A | 1 | Hanifa | −329 | −148 | −99 |
| Well-A | 2 | Tuwaiq | −336 | −149 | −103 |
| Well-A | 3 | Tuwaiq | −335 | −147 | −101 |
| Well-B | 1 | Jubaila | −272 | | |
| Well-B | 2 | Hanifa | −292 | −118 | −97 |
| Well-B | 3 | Hanifa | | | |

TABLE 3-continued

Deuterium isotopic data for Hanifa, Source T, and Jubaila formations and Well-A, Well-B, Well-C, Well-D, and Well-E exploratory wells

| Well | Sample No. | Source Rock Formation | δDC$_1$ | δDC$_2$ | δDC$_3$ |
|---|---|---|---|---|---|
| Well-B | 4 | Tuwaiq | −292 | −118 | −96 |
| Well-C | 1 | Jubaila | −265 | | |
| Well-C | 2 | Jubaila | −265 | | |
| Well-C | 3 | Jubaila | −266 | | |
| Well-C | 4 | Hanifa | −290 | −100 | |
| Well-C | 5 | Hanifa | | | |
| Well-C | 6 | Tuwaiq | −310 | −116 | |
| Well-C | 7 | Tuwaiq | −293 | −105 | −91 |
| Well-C | 8 | Tuwaiq | −294 | −113 | |
| Well-C | 9 | Tuwaiq | −306 | −118 | |
| Well-D | 1 | Jubaila | −224 | −128.0 | −105.0 |
| Well-D | 2 | Jubaila | −220 | −125.0 | −103.0 |
| Well-D | 3 | Jubaila | −223 | −130.0 | −105.0 |
| Well-D | 4 | Hanifa | −256 | −120.0 | −103.0 |
| Well-D | 5 | Tuwaiq | −278 | −110.0 | −96.0 |
| Well-D | 6 | Tuwaiq | −281 | −107.0 | −98.0 |
| Well-D | 7 | Tuwaiq | −281 | −109.0 | −97.0 |
| Well-D | 8 | Tuwaiq | −279 | −109.0 | −93.0 |
| Well-E | 1 | Jubaila | −225 | | |
| Well-E | 2 | Jubaila | −233 | | |
| Well-E | 3 | Jubaila | −229 | | |
| Well-E | 4 | Hanifa | −267 | | |
| Well-E | 5 | Hanifa | −273 | | |
| Well-E | 6 | Hanifa | −280 | | |
| Well-E | 7 | Tuwaiq | −277 | | |
| Well-E | 8 | Tuwaiq | −269 | | |
| Well-E | 9 | Tuwaiq | −270 | | |

As will be appreciated, thermal maturity may be used to evaluate the generative potential of source rock. One technique for estimating the thermal maturity of source rock is vitrinite reflectance (%% Ro). As used herein, the term "vitrinite" refers to a type of maceral that originates from the woody tissue of vascular plants. In some instances where vitrinite is unavailable or rare, such as carbonate depositional environments, the reflectance of solid bitumen or other vitrinite-like macerals may be used to estimate thermal maturity. In such instances, the resulting measurement of the reflectance of solid bitumen or other vitrinite-like macerals may be converted to a normalized vitrinite reflectance equivalent (VRo-eq). Alternatively, organic matter type and maturity may be determined using Rock Eval® or other pyrolysis techniques. For the exploration wells described in this example, present day thermal maturity was measured and calculated for all samples using Rock Eval® and solid bitumen optical reflectance techniques. Techniques such Rock Eval® or the determination of reflectance of vitrinite, bitumen, or other macerals requires the obtaining of core samples from the targeted formation.

Figure 3:
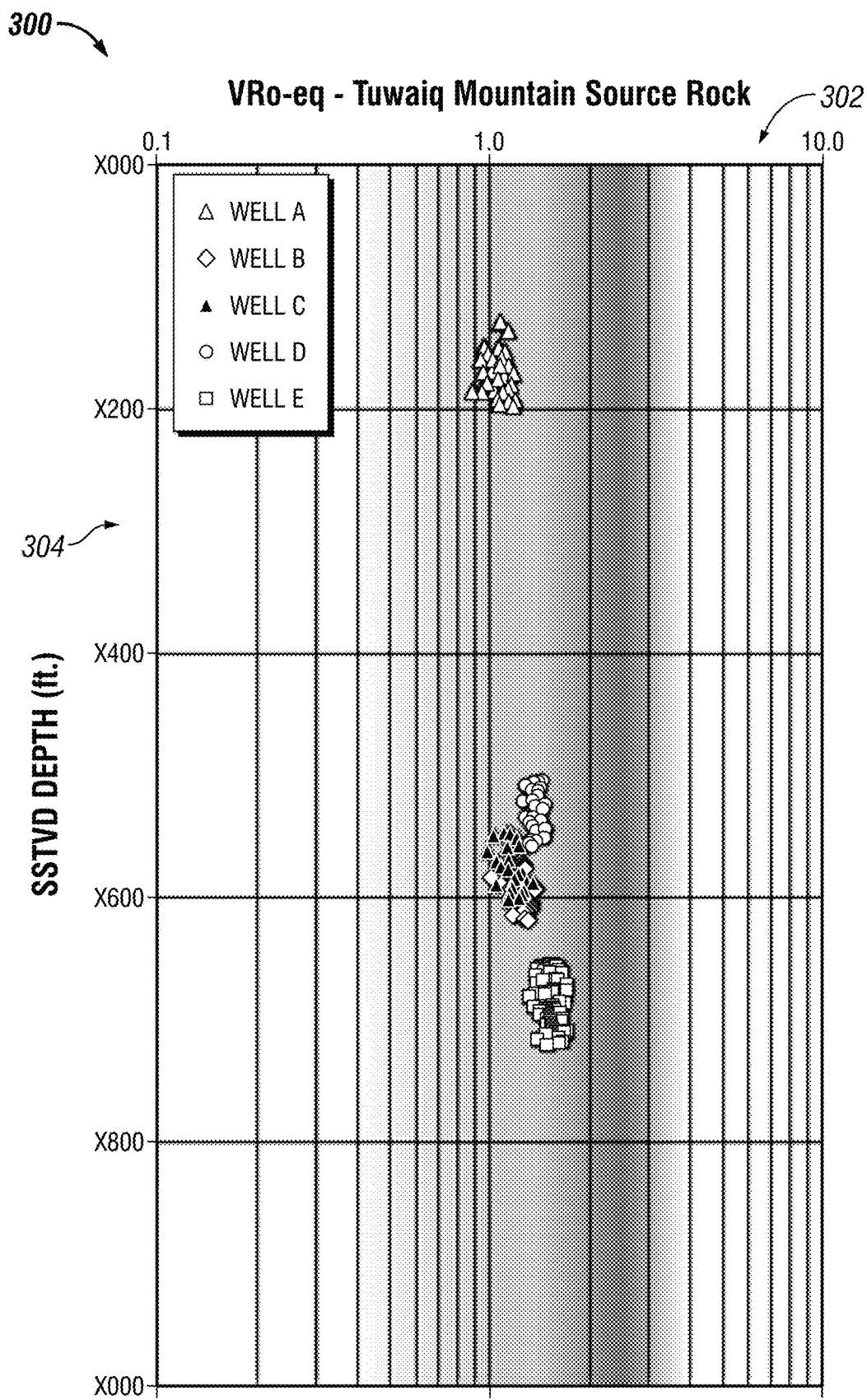
FIG. 3 is a plot of the vitrinite reflectance equivalent vs. depth for a first source rock formation in accordance with embodiments of the disclosure.

As discussed above, pyrolysis analysis techniques such as Rock Eval® may provide a determination of the temperature (Tmax) at which the maximum rate of hydrocarbon generation occurs in a kerogen sample. As shown in Table 1, the average Tmax value for Tuwaiq source rock is 475° C., with Tmax values as low as 455° C. in Well A and as high as 493° C. in Well E. These Tmax values suggest that the Tuwaiq source rock thermal maturity ranges between a late oil to early dry gas thermal maturity window. VRo-eq was estimated from Tmax data using the known Jarvie's conversion formula, as shown below in Equation 1:

$$\text{VRo-eq} = 0.018 \times T\text{max} - 7.16 \tag{1}$$

Where VRo-eq is the vitrinite reflectance equivalent and Tmax is the temperature at which the maximum rate of hydrocarbon generation occurs in a kerogen sample during pyrolysis analysis. The VRo-eq calculated for Tuwaiq source rock using Equation 1 ranged from 1.0% in Well-A to 1.55% in Well-E with an average VRo-eq of 1.39%. FIG. 3 is a plot 300 of the vitrinite reflectance equivalent determined by Equation 1 (on the x-axis 302) vs. depth (on the y-axis 304) for the Tuwaiq source rock. As shown in FIG. 3, a clear increase of VRo-eq with depth was observed.

Figure 4:
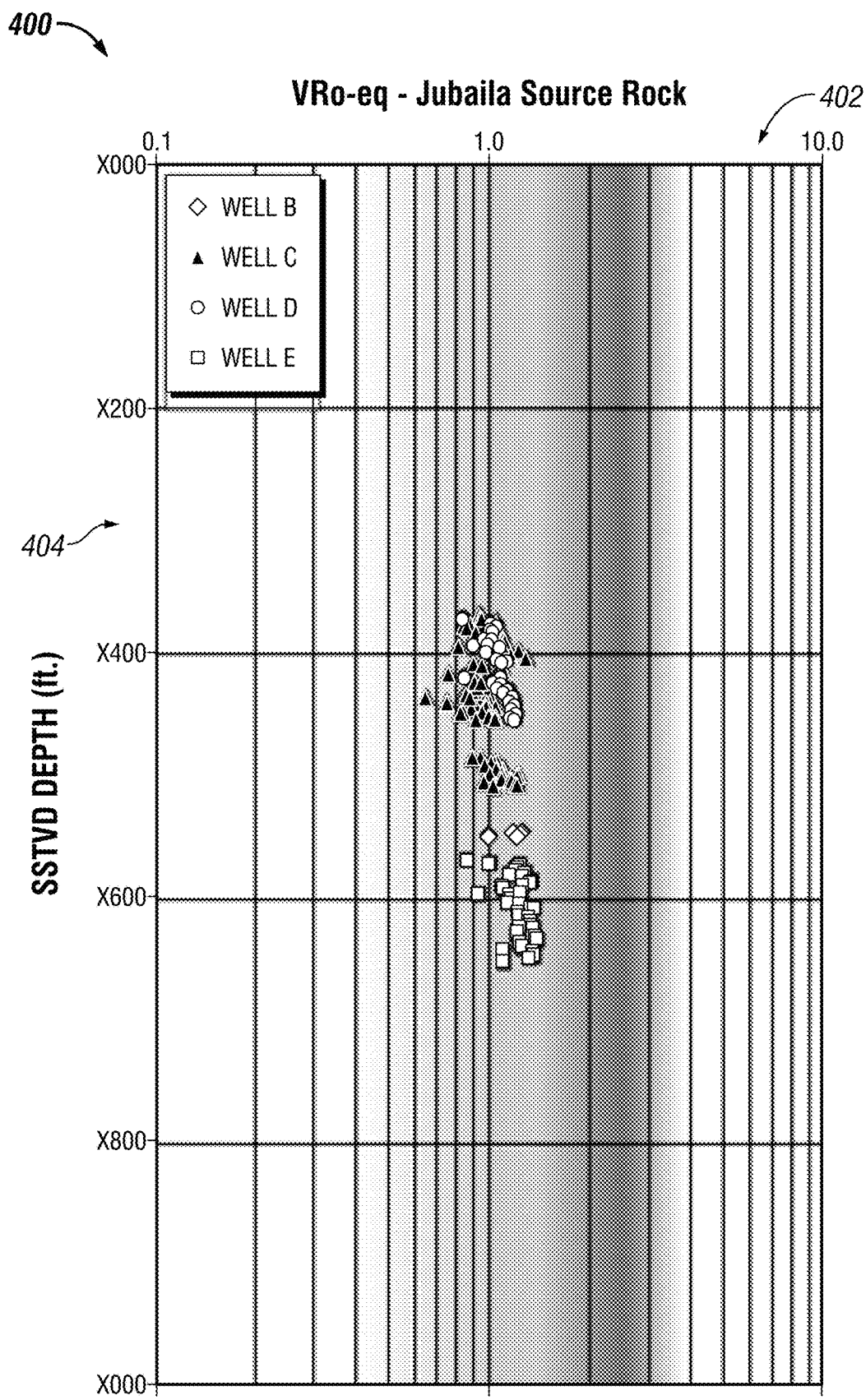
FIG. 4 is a plot of the vitrinite reflectance equivalent vs. depth for a second source rock formation in accordance with embodiments of the disclosure.

As shown in Table 1, the Jubaila source rock recorded an average TOC of 2.44% with a maximum of 4.98%. The hydrogen indices of organic matter in the formation rock are between 63 mg HC/g TOC and 231 mg HC/g TOC. As also shown in Table 1, the average Tmax value recorded for the Jubaila source rock was 462° C. with a Tmax as low as 453° C. for Well-A corresponding to an oil generation maturity window. A maximum average Tmax of 469° C. was recorded for the Jubaila source rock was recorded in Well-E, corresponding to a wet gas generation maturity window. The VRo-Eq calculated from Tmax according to Equation 1 ranged from 0.99% at Well-A to 1.28% at Well-E with an average VRo-eq of 1.1%. FIG. 4 is a plot 400 of the vitrinite reflectance equivalent (on the x-axis 402) determined by Equation 1 vs. depth (on the y-axis 404) for Well-B, Well-C, Well-D, and Well-E for the Jubaila source rock.

To confirm the VRo-eq determinations using the Jarvie conversion formula shown in Equation 1, the thermal maturity was also determined from solid bitumen (BitRo) fragments from Tuwaiq core samples. VRo-eq was estimated from solid bitumen reflectance (BitRo) using the known Jacob's conversion formula, as shown below in Equation 2:

$$\text{VRo-eq} = 0.618 \times \text{BitRo} - 0.4 \tag{2}$$

Where VRo-eq is the vitrinite reflectance equivalent and BitRo is the solid bitumen reflectance.

FIGS. 5A-5E depict bitumen reflectance data and images of representative core samples from Tuwaiq source rock for the five exploratory wells Well-A through Well-E. The measured samples were generally rick in organic matter content and included solid bitumen in various forms co-deposited with carbonate grains and, in some instances, associated with farmboidal pyrite. A network of amorphous bituminite and traces of inertinite was also observed in the sample matrix. For Well-E a small amount of organic particles corresponding to indigenous vitrinite were also encountered.

Figure 5A:
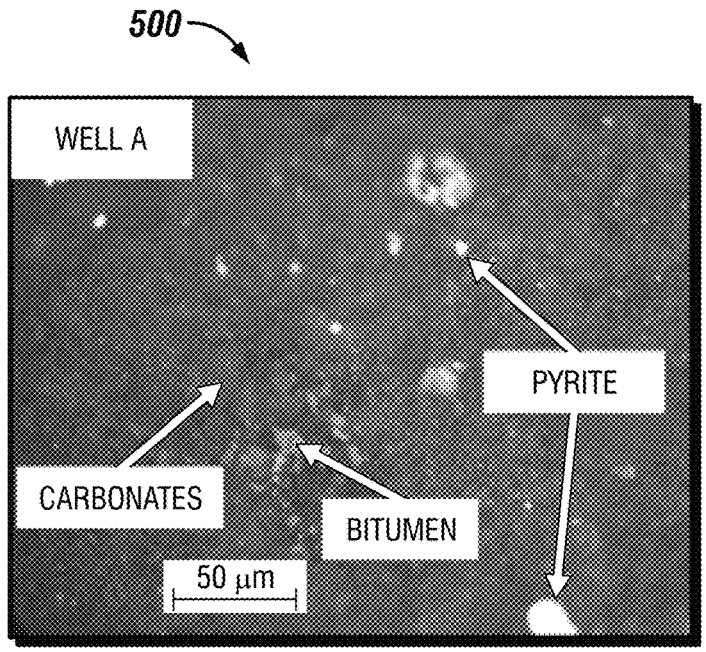
FIGS. 5A-5E are images of representative core samples and tables of bitumen reflectance data obtained from a source rock formation for five exploratory wells in a geographic region of interest in accordance with embodiments of the disclosure.

FIG. 5A depicts an image 500 of a representative core sample obtained from Well-A and a table 502 with the corresponding bitumen reflectance (BitRo) and VRo-eq values. As shown in FIG. 5A, the mean BitRo for a Tuwaiq source rock core sample at Well-A was 1.01% based on 28 readings, which resulted in a VRo-eq of 1.02% determined using Equation 2. Thus, the VRo-eq value calculated from BitRo is in agreement with the VRo-eq determined from Tmax using Equation 1. Both VRo-eq determination techniques suggest that the Tuwaiq source rock organic matter in Well-A is presently at a thermal maturity corresponding to the oil window of hydrocarbon generation.

Figure 5B:
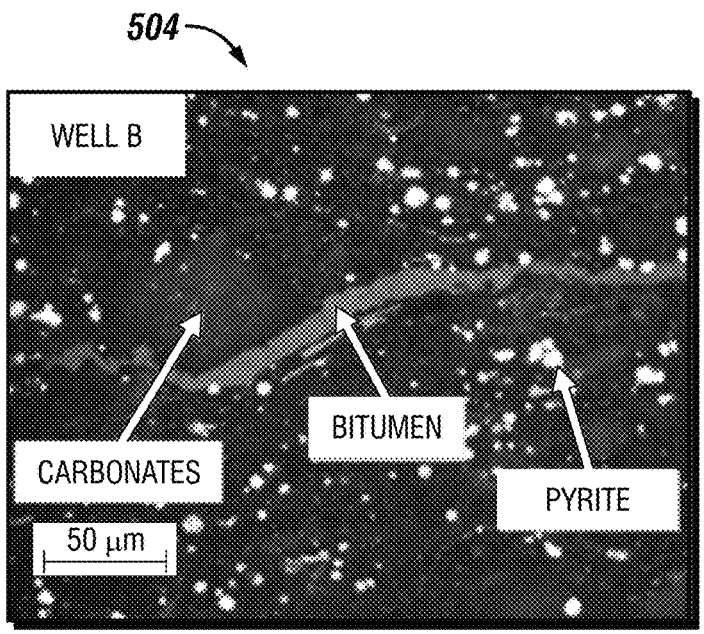

FIG. 5B depicts an image 504 of a representative core sample obtained from Well-B and a table 506 with the corresponding bitumen reflectance (BitRo) and VRo-eq values. As shown in FIG. 5B, the mean BitRo for a Tuwaiq source rock core sample at Well-B was 1.5% based on 38 readings, which resulted in a VRo-Eq of 1.33% determined using Equation 2. Here again, the VRo-Eq value calculated from BitRo is in agreement with the VRo-Eq determined from Tmax using Equation 1. Both VRo-Eq determination techniques suggest that the Tuwaiq source rock organic matter in Well-B is presently at the wet gas window of hydrocarbon generation.

Figure 5C:
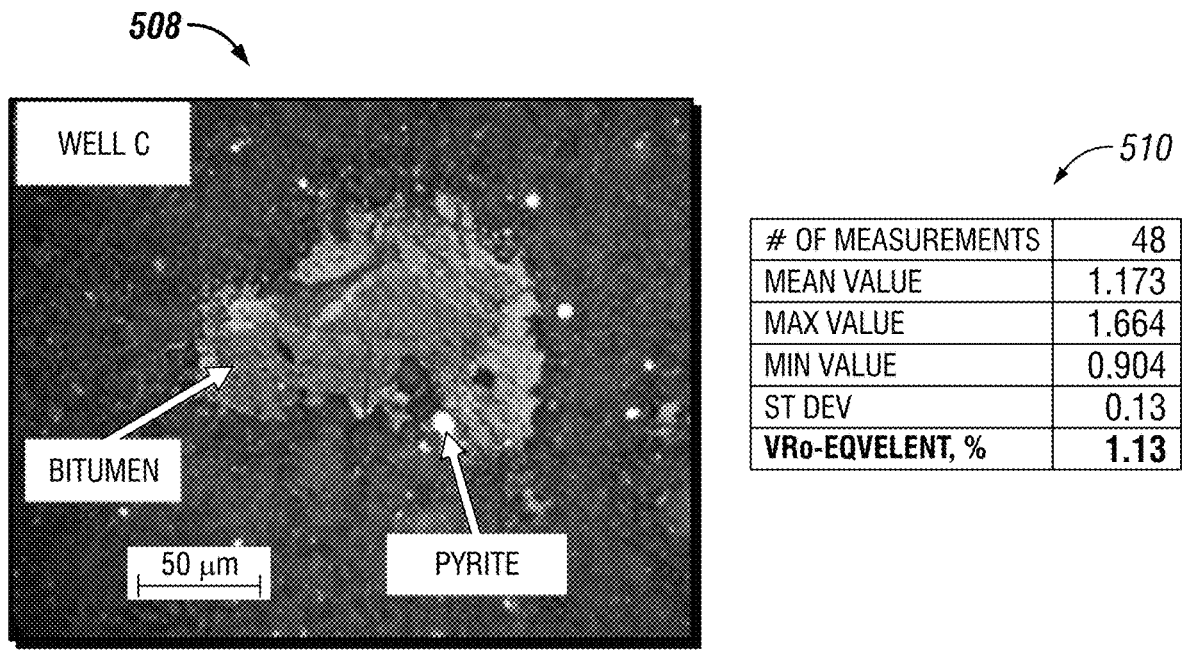

FIG. 5C depicts an image 508 of a representative core sample obtained from Well-C and a table 510 with the corresponding bitumen reflectance (BitRo) and VRo-eq value. As shown in FIG. 5C, the mean BitRo for a Tuwaiq source rock core sample at Well-C was 1.2% based on 48 readings, which resulted in a VRo-Eq of 1.13% determined using Equation 2. The VRo-Eq value calculated from BitRo is again comparable to the VRo-Eq determined from Tmax using Equation 1. Both VRo-Eq determination techniques suggest that the Tuwaiq source rock organic matter in Well-C is presently at the late oil window of hydrocarbon generation.

Figure 5D:
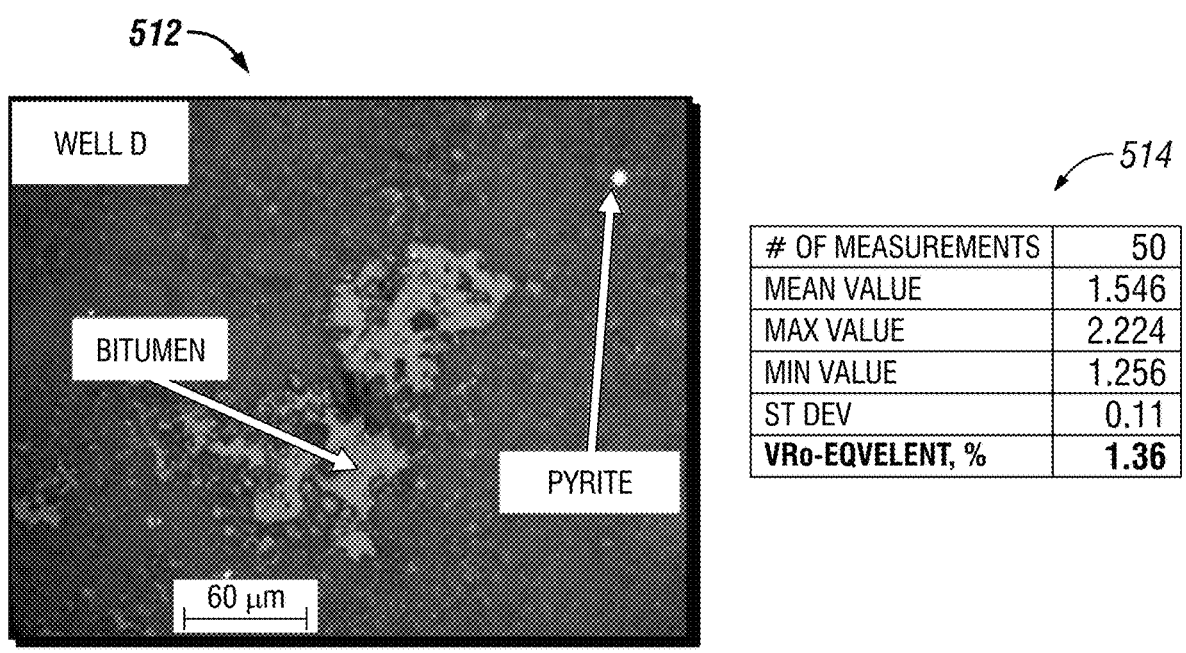

FIG. 5D depicts an image 512 of a representative core sample obtained from Well-D and a table 514 with the corresponding bitumen reflectance (BitRo) and VRo-eq value. As shown in FIG. 5D, the mean BitRo for a Tuwaiq source rock core sample at Well-D was 1.54% based on 50 readings, which resulted in a VRo-Eq of 1.36% determined using Equation 2. For Well-D, the VRo-Eq value calculated from BitRo is again comparable to the VRo-Eq determined from Tmax using Equation 1. Both VRo-Eq determination techniques suggest that the Tuwaiq source rock organic matter in Well-D is presently at the late wet gas window of hydrocarbon generation.

Figure 5E:
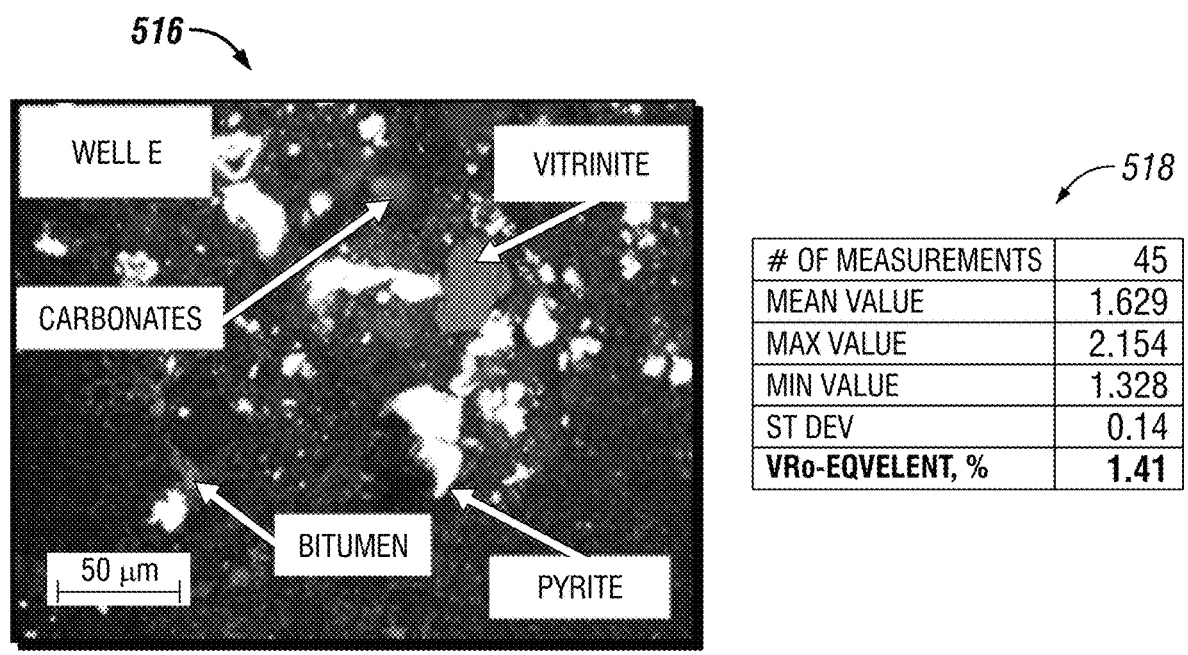

FIG. 5E depicts an image 516 of a representative core sample obtained from Well-E and a table 518 with the corresponding bitumen reflectance (BitRo) and VRo-eq value. As shown in FIG. 5E, the mean BitRo for a Tuwaiq source rock core sample at Well-E was 1.63% based on 45 readings, which resulted in a VRo-Eq of 1.36% determined using Equation 2. The VRo-Eq determined from Tmax using Equation 1 was about 1.55% different than the VRo-Eq determined from the BitRo value. As such, one of the VRo-Eq estimation techniques may be less sensitive at slightly higher thermal maturities. As mentioned above, however, organic particles of indigenous vitrinite were obtained in Well-E. Using these particles, the mean % Ro of the primary vitrinite was determined to be 1.5% based on 6 measurements. Thus, the % Ro value determined from the primary vitrinite shows a better correlation with the VRo-Eq determined from Tmax (1.55%) than the VRo-Eq determined from BitRo (1.36%). The thermal maturity measured from primary vitrinite and determined from Tmax according to Equation 1 indicate that the Tuwaiq source rock organic matter in Well-E is very mature and at the dry gas window of hydrocarbon generation.

Figure 6:
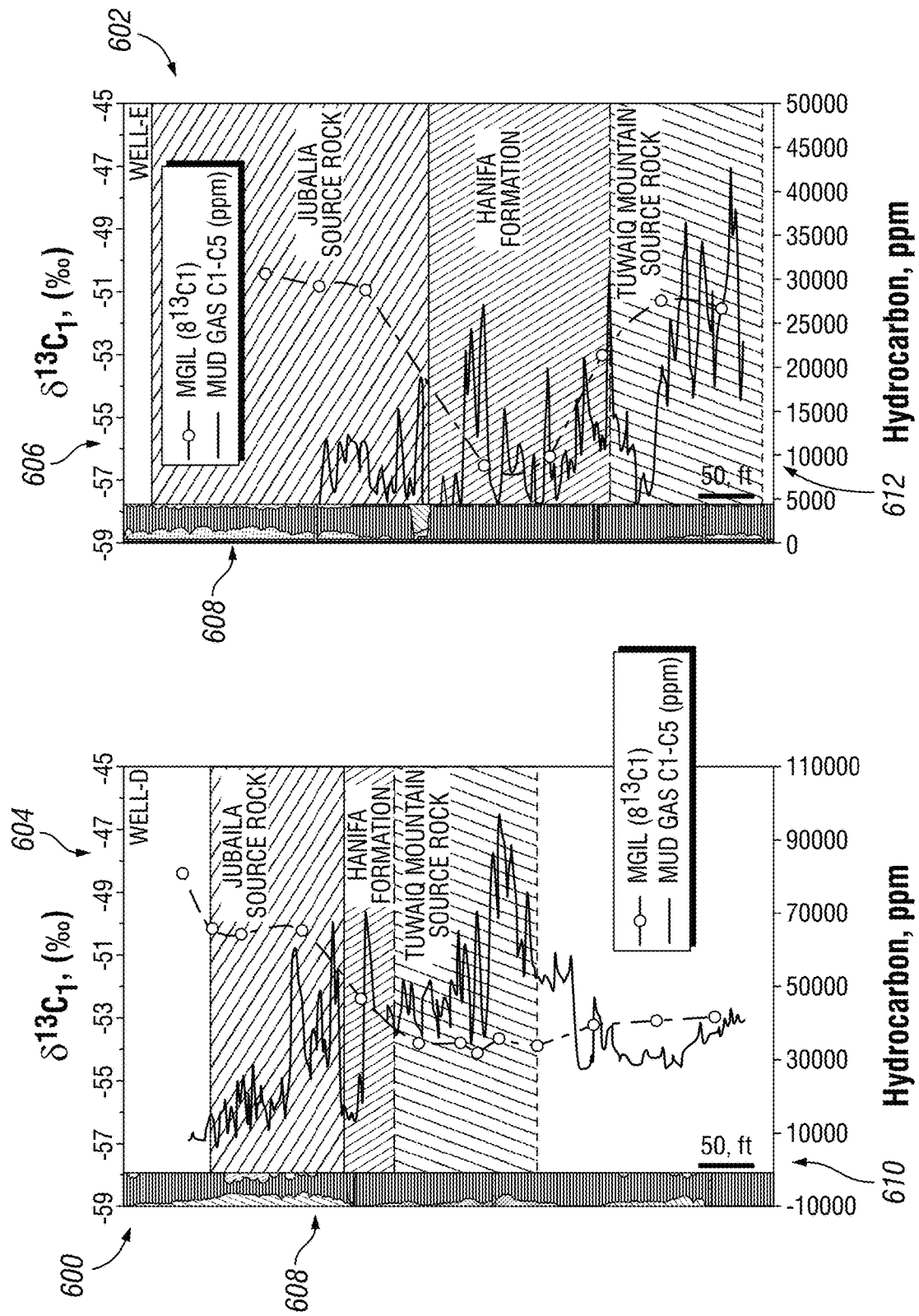
FIG. 6 is a side-by-side depth plot of geological data for two exploration wells in a geological region of interest in accordance with embodiments of the disclosure.

FIG. 6 depicts side-by-side depth plots for exploration wells Well-D and Well-E and illustrates general geological data with gas sampling locations. The plot 600 depicts geological data for Well-D and the plot 602 depicts geological data for Well-E. Each plot 600 and 602 depicts the measured methane carbon isotopic values ($\delta^{13}C_1$ on the upper x-axes 604 and 606) vs depth (on the y-axes 608) and the recorded well site drilling mud gas (C1-C5 total gas) measurements (on the lower x-axes 610 and 612) vs. depth. The y-axes 608 depict depths of 550 ft from the same starting depth and encompassing all three source rock targets Jubaila, Hanifa, and Tuwaiq.

FIG. 6 illustrates the depth variations between the two wells across more than 80 kilometers (km) of the basin, for which the depth differential in Tuwaiq is only about 170 ft and suggestive of a wide shallow geological basin. The mud gas measurements on the x-axes 610 and 612 illustrate, for each of Jubaila and Tuwaiq source rock, stronger gas shows towards the basal sections. This data is typical of transgressive depositional cycles where the richest organic matter and the higher derived gas shows may be found within each formation.

As noted above, the upper x-axes 604 and 606 depicted in FIG. 6 show the measured methane carbon isotopic values for each gas sampling location, and the plots 600 and 602 depict the interpolated trend of methane carbon isotopic values. In general, isotopic trends with increasing depth generally result in less negative isotopic values due to progressive generation of isotopically heaver methane gas via thermal cracking of indigenous kerogen. However, as shown in FIG. 6, for Well-D the shallower Jubaila methane carbon isotopic values are significantly less negative than the deeper Tuwaiq source rock, suggesting a distinct difference between the Jubaila and Tuwaiq source organic matter. As also shown in the plot 602 in FIG. 6, for Well-E there were no observed significant differences between the Jubaila and Tuwaiq source rock formations. However, the Tuwaiq methane gas isotopic values for Well-E have increased over those from Well-D, likely as a result of the higher geothermal gradient observed in the vicinity of Well-E.

Using the Tuwaiq source rock data from Table 1 and the gas isotope data from Table 2 from nearly equivalent depth intervals, accurate thermal maturity relationships were established between the thermal maturity (as indicated by VRo-Eq) and the gas isotope data. Table 3 depicts the thermal maturity calibration data taken from Tables 1 and 2. As discussed above, the VRo-Eq from Tmax was calculated according to Equation 1, and the VRo-Eq from bitumen reflectance was calculated according to Equation 2. As also discussed above, samples having primary vitrinite were obtained from Well-E and used to directly measure vitrinite reflectance using optical measurements. The fifth column of Table 4 depicts the directly measured vitrinite reflectance:

TABLE 4

Vitrinite reflectance equivalents, vitrinite reflectance, and isotopic values

| Well | Tmax | VRo-Eq from Tmax | VRo-Eq from solid bitumen | Vitrinite Reflectance (% Ro) | $\delta^{13}C_1$ | $\delta DC_1$ |
|---|---|---|---|---|---|---|
| Well A | 455 | 1.03 | 1.02 | NA | −59.7 | −336 |
| Well C | 465 | 1.21 | 1.14 | NA | −55.8 | −301 |
| Well B | 472 | 1.34 | 1.33 | NA | −56.3 | −292 |
| Well D | 477 | 1.43 | 1.36 | NA | −53.9 | −280 |
| Well E | 484 | 1.55 | 1.40 | 1.5 | −51.4 | −273 |

As shown in Table 4, the comparison between the three vitrinite reflectance (i.e., Tmax-based vitrinite reflectance equivalence, bitumen-based vitrinite reflectance equivalence, and directly measured vitrinite reflectance) values indicates a high confidence in the thermal maturity determinations. The relationship between the vitrinite reflectance (as an indicator of thermal maturity) and the measured gas isotopic values of entrained generated hydrocarbon gases may be used to develop a thermal maturity determination based on isotopic data.

Figure 7:
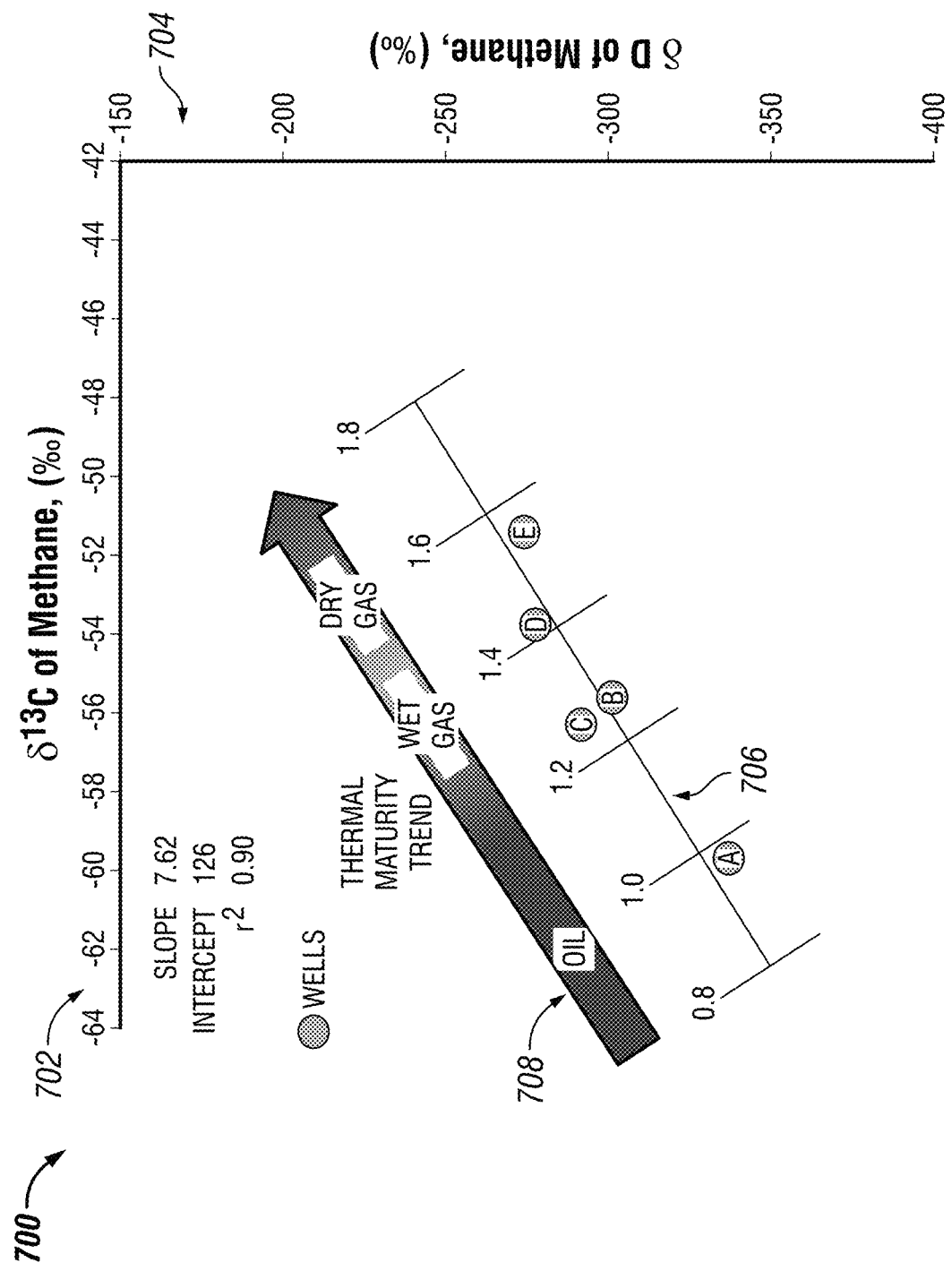
FIG. 7 is a plot of methane carbon and deuterium isotopic data and vitrinite reflectance for a source rock formation in a geological region of interest in accordance with embodiments of the disclosure.

FIG. 7 is a plot 700 illustrating the relationship between methane carbon-13 ($\delta^{13}C_1$) and deuterium ($\delta DC_1$) isotopic data, and vitrinite reflectance based on the values from Table 3. The plot 700 depicts methane carbon-13 (on the x-axis 702) and deuterium (on the y-axis 704), with the vitrinite reflectance values for each of Well-A, Well-B, Well-C, Well-D, and Well-E plotted along the line 706. As shown by arrow 708, the increasing vitrinite reflectance values correspond to an increasing thermal maturity trend (e.g., from oil to wet gas to dry gas).

In some embodiments, a least squared regression analysis may be applied to the data in Table 3 to determine the relationship between the vitrinite reflectance (as an indicator of thermal maturity) and the measured gas isotopic values of entrained generated hydrocarbon gases. In some embodiments, a relationship between the vitrinite reflectance and methane carbon-13 isotope may be determined. For example, for the Tuwaiq source rock, the least squares regression analysis yielded a correlation coefficient (r2) value of 0.9 for the relationship between the vitrinite reflectance equivalent and methane carbon-13 isotope, such that the relationship may be defined according to Equation 3:

$$VRo\text{-}Eq = 0.069 \times \delta^{13}C_1 + 5.13 \qquad (3)$$

Where VRo-Eq is the vitrinite reflectance equivalent and $\delta^{13}C_1$ is the isotopic value of methane carbon-13 as determined from MGIL data. A similar relationship between vitrinite reflectance equivalent and methane deuterium may also be determined using a least squares regression analysis or other suitable analysis.

The gas isotopic thermal maturity model depicted in Equation 3 may be used to determine vitrinite reflectance equivalence (and, thus, thermal maturity) in source rock and identify "sweet spots" for drilling. For example, the determination of thermal maturity from isotopic values may be developed and used in locations where no or few reliable source rock samples are available, or in situations (for example, tight gas plays) where only captured hydrocarbon gases are feasible for extraction. Thus, the thermal maturity determined from gas isotopic values may be used to evaluate thermal maturities and the production potential of development wells in such locations.

Processes and Systems for Thermal Maturity Determinations

Figure 8:
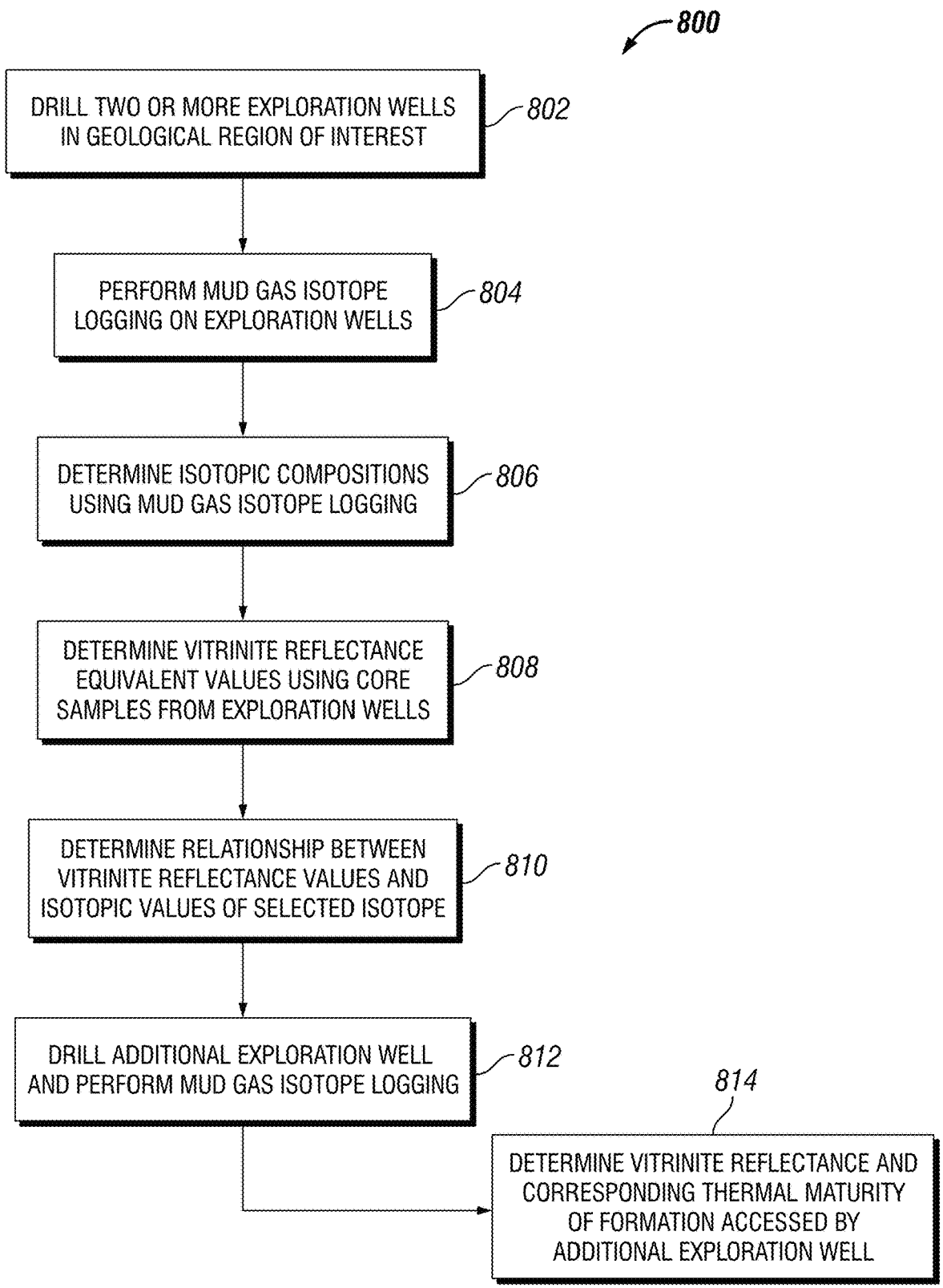
FIG. 8 is a block diagram of a process for determining thermal maturity from gas isotopic values obtained from mud gas isotope logging (MGIL) in accordance with embodiments of the disclosure.

FIG. 8 depicts a process 800 for determining thermal maturity from gas isotopic values obtained from mud gas isotope logging (MGIL) in accordance with an embodiment of the disclosure. Initially, two or more exploration wells may be drilled into a geological region of interest (block 802). For example, the exploration wells may traverse multiple source rock formations at different depths in the geological region of interest.

During drilling of the wells, mud gas isotope logging may be performed on the exploration wells (block 804). The isotopic values in mud gas may be determined using mud gas isotope logging (block 806), as discussed above. For example, in some embodiments, the isotopic values may include carbon-13 and deuterium isotopic values in mud gases such as methane, ethane, propane, i-butane, n-butane, i-pentane, and n-pentane.

Next, vitrinite reflectance equivalent (VRo-Eq) values may be determined using core samples from the exploration wells using known techniques. For example, in some embodiments, vitrinite reflectance equivalent values may be determined from the temperature (Tmax) at which the maximum rate of hydrocarbon generation occurs in a kerogen sample during pyrolysis analysis, as discussed above and shown in Equation 1. Additionally or alternatively, in some embodiments, vitrinite reflectance equivalent values may be determined using bitumen reflectance, as discussed above and shown in Equation 2.

Next, a relationship between vitrinite reflectance equivalent (and thermal maturity) and the isotopic values for a selected isotope may be determined (block 810). For example, the selected isotope may be carbon-13 and the isotopic values may be methane carbon-13. In other embodiments, other isotopes and isotopic values may be used. In some embodiments, the selected isotope may be deuterium and the isotopic values may be methane deuterium, ethane deuterium, or propane deuterium. In some embodiments, the selected isotope may be carbon-13 and the isotopic values may be ethane carbon-13, propane carbon-13, i-butane carbon-13, n-butane carbon-13, i-pentane carbon-13, or n-pentane carbon-13.

The vitrinite reflectance equivalent (as an indicator of thermal maturity) may then be determined from isotopic values subsequently obtained from mud gas isotope logging data. For example, as shown in FIG. 8, another exploration well may be drilled and mud gas isotope logging may be performed on the well (block 812). Using the mud gas isotope logging data, the vitrine reflectance and the corresponding thermal maturity of the well may be determined (block 814). In some embodiments, the vitrinite reflectance equivalent may be compared to a range of vitrinite reflectance values that correspond to different thermal maturities. For example, a vitrinite reflectance value in the range of about 0.8 to about 1.3 may indicate a thermal maturity of oil, a vitrinite reflectance value in the range of greater than about 1.3 to about 1.5 may indicate a thermal maturity of wet gas, and a vitrinite reflectance value in the range of greater than about 1.5 may indicate a thermal maturity of dry gas.

The vitrinite reflectance and corresponding thermal maturity may thus be determined from isotopic values without obtaining a core sample or performing other time-consuming and costly procedures that require additional trips downhole. As discussed above, the mud gas isotope logging may be performed on return mud during drilling the additional exploration, thus enabling near real-time determination of vitrinite reflectance and corresponding thermal maturity for formations encountered at various depths during drilling. In some embodiments, lateral drilling operations may use mud gas isotope logging and the determination of vitrinite reflectance and corresponding thermal maturity to assess the effectiveness of hydraulic fracturing treatments in a formation and to ensure maximum in-zone completions to optimize production potential.

Figure 9:
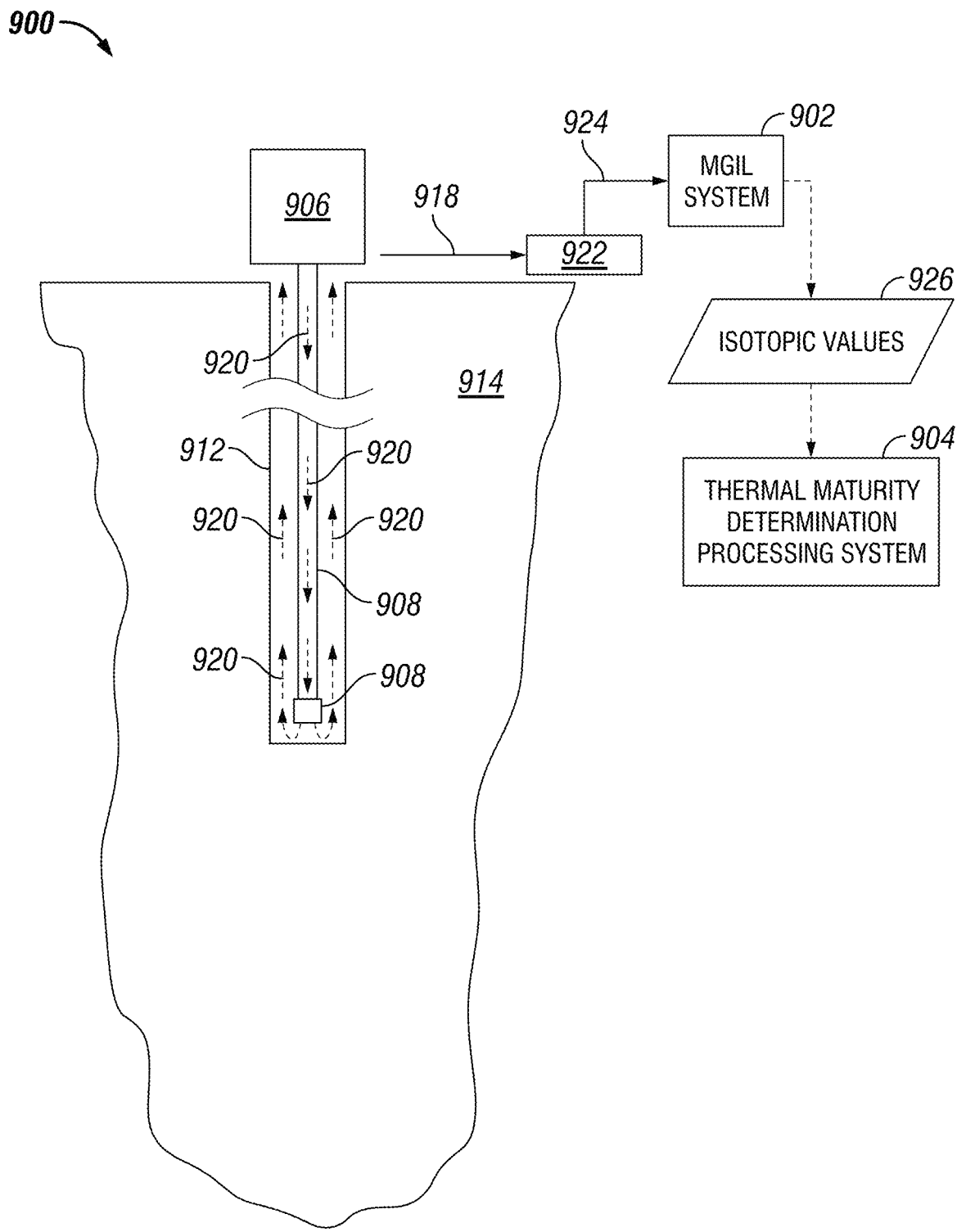
FIG. 9 is a block diagram of a well site having a mud gas isotope logging system and a thermal maturity determination system in accordance with an embodiment of the disclosure.

FIG. 9 depicts a well site 900 having a mud gas isotope logging (MGIL) system 902 and a thermal maturity determination processing system 904 in accordance with an embodiment of the disclosure. The drilling environment includes a drilling system 906 configured to operate a drill 908 connected to a drill pipe 910 extending into a wellbore 912 (also referred to as a "borehole") formed in a shale formation 914. Although FIG. 9 depicts the wellbore 912 and the drilling system 906 in a generally vertical orientation, it should be appreciated that in other embodiments other orientations may be used.

The wellbore 912 may include any form of a hole formed in a geologic formation. In some embodiments, the wellbore 912 may include a wellbore created for the purpose of locating and extracting hydrocarbons or other resources from the formation 916. For example, the formation 916 may include an oil and gas reservoir, and the wellbore 912 may include a wellbore drilled into the formation 916 for the purpose of locating and obtaining information about the oil, gas and other hydrocarbons in the reservoir.

As will be appreciated, a drilling mud (also referred to as a "drilling fluid") may be circulated around the drill 908 via the drill pipe 910 and the wellbore 912, as shown by arrows 918, to lubricate the drill 908 and remove cuttings generated by drilling into the formation 916. The drilling mud may return to the surface, as shown by arrow 920, for collection and processing, as shown by block 922. The collection and processing of the return drilling mud may include various components that remove solids such as cuttings from the return mud. The collection and processing may include also include a degasser that removes gases 924 from the return mud. The gas removed from the return mud may be collected or sampled via the mud gas isotope logging system 902. The mud gas isotopic logging system 902 may analyze the gases 924 removed from the drilling mud and determine the isotopic values 926 of the gases. For example, the mud gas isotopic logging system 902 may include an isotope ratio mass spectrometer (IRMS) for analyzing mud gases removed from the drilling mud.

The isotopic values 926 may be processed by a thermal maturity determination processing system 904 to determine an isotopic maturity model in accordance with embodiments of the disclosure. In some embodiments, the thermal maturity determination processing system 904 may include for example, a processor, a memory, and a display. The processor (as used the disclosure, the term "processor" encompasses microprocessors) may include one or more processors having the capability to receive and process data received from the mud gas isotopic logging system 902. The processor may also include single-core processors and multicore processors and may include graphics processors.

The thermal maturity determination processing system 904 may also include a memory (which may include one or more tangible non-transitory computer readable storage mediums) that may include volatile memory, such as random access memory (RAM), and non-volatile memory, such as ROM, flash memory, a hard drive, any other suitable optical, magnetic, or solid-state storage medium, or a combination thereof. The memory of the thermal maturity determination processing system 904 may store executable computer code that may include, for example, executable computer code for processing data received from the mud gas isotopic logging system 902 and displaying data received from the mud gas isotopic logging system 902, such as on a display of the thermal maturity determination processing system 904.

Accordingly, the mud gas isotopic logging system 902 may also include a display, such as a liquid crystal display (LCD), an organic light emitting diode (OLED) display, or other suitable display. The display may display a user interface (for example, a graphical user interface) that may enable a user to obtain and view data from the thermal maturity determination processing system 904. In some embodiments, the thermal maturity determination processing system 904 may include a touch screen display and may include or be provided with touch sensitive elements through which a user may interact with the user interface.

In some embodiments, the thermal maturity determination processing system 904 may include a network interface that provides for communication between the thermal maturity determination processing system 904 and other computers remote from the well site 900. Such a network interface may include a wired network interface card (NIC), a wireless (e.g., radio frequency) network interface card, or combination thereof. In some embodiments, the thermal maturity determination processing system 904 may provide for the transmission of vitrinite reflectance relationships and determinations to another computer remote from a well site.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described herein. It is to be understood that the forms shown and described herein are to be taken as examples of embodiments. Elements and materials may be substituted for those illustrated and described herein, parts and processes may be reversed or omitted, and certain features may be utilized independently, all as would be apparent to one skilled in the art after having the benefit of this description. Changes may be made in the elements described herein without departing from the spirit and scope of the disclosure as described in the following claims. Headings used herein are for organizational purposes only and are not meant to be used to limit the scope of the description.

What is claimed is:

1. A method for determining the thermal maturity of a first rock formation in a geological region of interest for hydrocarbon production, comprising:
   drilling a plurality of exploration wells to access the first rock formation;
   obtaining mud gas isotope logging data for each of the plurality of exploration wells, the mud gas isotope logging data comprising first isotopic values associated with an isotope in a mud gas;
   obtaining a plurality of first vitrinite reflectance equivalent values for each of the plurality of exploration wells;
   determining, using the plurality of first vitrinite reflectance equivalent values, a relationship between vitrinite reflectance equivalent and the first isotopic values;
   determining a second vitrinite reflectance equivalent value using the relationship and second isotopic values associated with an additional exploration well accessing a second rock formation; and
   identifying a thermal maturity of the second rock formation using the second vitrinite reflectance equivalent value determined from the second isotopic values associated with the additional exploration well accessing a second rock formation.

2. The method of claim 1, comprising identifying a drilling location in the geological region of interest for hydrocarbon production using the thermal maturity indicated by the vitrinite reflectance equivalent.

3. The method of claim 1, wherein the mud gas comprises methane and the isotope comprises carbon-13.

4. The method of claim 1, wherein the mud gas comprises hydrogen and the isotope comprises deuterium.

5. The method of claim 1, wherein obtaining the vitrinite reflectance equivalent for each of the plurality of exploration wells comprises:
   determining, for each of the plurality of exploration wells, a temperature at which the maximum rate of hydrocarbon generation occurs in a kerogen sample from the respective exploration well during a pyrolysis analysis; and
   calculating the vitrinite reflectance equivalent from the temperature for each of the plurality of exploration wells.

6. The method of claim 1, wherein obtaining the vitrinite reflectance equivalent for each of the plurality of exploration wells comprises:
   determining an amount of bitumen in a core sample obtained from the respective exploration well; and
   calculating the vitrinite reflectance equivalent from the bitumen amount for each of the plurality of exploration wells.

7. The method of claim 1, wherein determining a relationship between vitrinite reflectance equivalent and the isotopic values comprises performing a least squares regression analysis on a set of vitrinite reflectance equivalent values and a set of isotopic values.

8. A system for determining the thermal maturity of a first rock formation in a geological region of interest for hydrocarbon production, the system comprising:
- a mud gas isotope logging system configured to receive mud gas and determine isotopic values of associated with an isotope in the mud gas;
- a thermal maturity determination processing system comprising a processor and a non-transitory computer-readable memory accessible by the processor, the memory having executable code stored thereon, the executable code comprising a set of instructions that causes the processor to perform operations comprising:
- receiving, from the mud gas isotope logging system, mud gas isotope logging data for each of a plurality of exploration wells, the mud gas isotope logging data comprising first isotopic values associated with the isotope in the mud gas;
- obtaining a plurality of first vitrinite reflectance equivalent values for each of the plurality of exploration wells, the plurality of first vitrinite reflectance equivalent values determined from a core sample from each of the plurality of exploration wells;
- determining, using the plurality of first vitrinite reflectance equivalent values, a relationship between vitrinite reflectance equivalent and the first isotopic values;
- determining a second vitrinite reflectance equivalent value using the relationship and second isotopic values associated with an additional exploration well accessing a second rock formation; and
- identifying a thermal maturity of the second rock formation using the second vitrinite reflectance equivalent value determined from the second isotopic values associated with the additional exploration well accessing a second rock formation.

9. The system of claim 8, wherein the mud gas comprises methane and the isotope comprises carbon-13.

10. The system of claim 8, wherein the mud gas comprises hydrogen and the isotope comprises deuterium.

11. The system of claim 8, wherein obtaining a vitrinite reflectance equivalent for each of the plurality of exploration wells comprises:
- determining, for each of the plurality of exploration wells, a temperature at which the maximum rate of hydrocarbon generation occurs in a kerogen sample from the respective exploration well during a pyrolysis analysis; and
- calculating the vitrinite reflectance equivalent from the temperature for each of the plurality of exploration wells.

12. The system of claim 8, wherein obtaining a vitrinite reflectance equivalent for each of the plurality of exploration wells comprises:
- determining an amount of bitumen in a core sample obtained from the respective exploration well; and
- calculating the vitrinite reflectance from the bitumen amount for each of the plurality of exploration wells.

13. The system of claim 8, wherein determining a relationship between vitrinite reflectance equivalent and the isotopic values comprises performing a least squares regression analysis on a set of vitrinite reflectance equivalent values and a set of isotopic values.

14. A method for determining the thermal maturity of a rock formation in a geological region of interest for hydrocarbon production, comprising:
- obtaining a carbon-13 isotopic value from a mud gas isotope logging system, the carbon-13 isotopic value associated with a mud gas;
- determining a vitrinite reflectance equivalent from the carbon-13 isotopic value; and
- comparing the vitrinite reflectance equivalent to a range of vitrinite reflectance values to identify a thermal maturity of the rock formation.

15. The method of claim 14, wherein the mud gas comprises methane.

16. The method of claim 14, comprising identifying a drilling location in the geological region of interest for hydrocarbon production using the thermal maturity.

* * * * *